(12) United States Patent
Yang et al.

(10) Patent No.: US 11,520,647 B2
(45) Date of Patent: Dec. 6, 2022

(54) AGRICULTURAL SENSOR PLACEMENT AND FAULT DETECTION IN WIRELESS SENSOR NETWORKS

(71) Applicant: THE TEXAS A&M UNIVERSITY SYSTEM, College Station, TX (US)

(72) Inventors: Yanxiang Yang, College Station, TX (US); Jiang Hu, College Station, TX (US); Dana O. Porter, Wolforth, TX (US); Thomas H. Marek, Amarillo, TX (US); Charles C. Hillyer, Amarillo, TX (US); Lijia Sun, College Station, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 118 days.

(21) Appl. No.: 16/771,320

(22) PCT Filed: Dec. 11, 2018

(86) PCT No.: PCT/US2018/064942
§ 371 (c)(1),
(2) Date: Jun. 10, 2020

(87) PCT Pub. No.: WO2019/118453
PCT Pub. Date: Jun. 20, 2019

(65) Prior Publication Data
US 2020/0387419 A1 Dec. 10, 2020

Related U.S. Application Data

(60) Provisional application No. 62/597,044, filed on Dec. 11, 2017.

(51) Int. Cl.
*G06F 11/07* (2006.01)
*G01N 33/24* (2006.01)
*G05B 19/042* (2006.01)

(52) U.S. Cl.
CPC ....... *G06F 11/0709* (2013.01); *G01N 33/246* (2013.01); *G05B 19/042* (2013.01);
(Continued)

(58) Field of Classification Search
CPC ............. G06F 11/0709; G06F 11/0751; G06F 11/0778; G01N 33/246; G01N 2033/245;
(Continued)

(56) References Cited

U.S. PATENT DOCUMENTS 6,006,604 A * 12/1999 Rabelo .................. G01F 23/802
73/304 C

FOREIGN PATENT DOCUMENTS

| CN | 103024758 A | * | 4/2013 |
| CN | 103024758 | | 5/2015 |
| CN | 105557388 B | * | 10/2016 |

OTHER PUBLICATIONS

International Search Report and Written Opinion dated May 1, 2019 for PCT Patent Application No. PCT/US2018/064942.
(Continued)

*Primary Examiner* — Chad G Erdman
(74) *Attorney, Agent, or Firm* — Thomas | Horstemeyer, LLP

(57) ABSTRACT

Disclosed are various embodiments for optimized sensor deployment and fault detection in the context of agricultural irrigation and similar applications. For instance, a computing device may execute a genetic algorithm (GA) routine to determine an optimal sensor deployment scheme such that a mean-time-to-failure (MTTF) for the system is maximized, thereby improving communication of sensor measurements. Moreover, in various embodiments, a centralized fault detection scheme may be employed and a soil moisture of a
(Continued)

field can be determined by statistically inferring soil moistures at locations of faulty nodes using spatial and temporal correlations.

17 Claims, 13 Drawing Sheets

(52) U.S. Cl.
CPC ...... *G06F 11/0751* (2013.01); *G06F 11/0778* (2013.01); *G01N 2033/245* (2013.01); *G05B 2219/2625* (2013.01)

(58) Field of Classification Search
CPC ......... G05B 19/042; G05B 2219/2625; H04W 16/18; H04W 84/18; G06N 3/126
See application file for complete search history.

(56) References Cited

OTHER PUBLICATIONS

Romoozi; et al. "A positioning method in wireless sensor networks using genetic algorithms." Physics Procedia 33 (2012): 1042-1049.
Ferentinos; et al. "Adaptive design optimization of wireless sensor networks using genetic algorithms." Computer Networks 51.4 (2007): 1031-1051.
Carter, ; et al. "A probabilistic model for the deployment of sensors." 2009 IEEE Sensors Applications Symposium. IEEE, 2009.

\* cited by examiner

AGRICULTURAL SENSOR PLACEMENT AND FAULT DETECTION IN WIRELESS SENSOR NETWORKS

CROSS-REFERENCE TO RELATED-APPLICATIONS

This application is the § 371 national phase application of PCT/US2018/064942, filed Dec. 11, 2018, which claims the benefit of and priority to U.S. Provisional Patent Application No. 62/597,044 entitled "AGRICULTURAL SENSOR PLACEMENT AND FAULT DETECTION IN WIRELESS SENSOR NETWORKS," filed Dec. 11, 2017, the contents of which being incorporated by reference in their-entireties herein.

BACKGROUND

Fresh water is an essential necessity for life. However, as a resource, water supplies are over-stressed by the growing human population and fluctuations in climate. Agricultural irrigation accounts for two-thirds of global fresh water use and therefore plays a pivotal role in water savings. Traditionally, irrigation is controlled by manual scheduling. That is, a fixed amount of water is irrigated periodically where the period is manually decided by users. Soil moisture sensors can considerably help improve water use efficiency of irrigation.

SUMMARY OF THE INVENTION

According to a first embodiment, a system for determining an optimal placement of sensors in a field to form a sensor network is described where the system includes at least one computing device and program instructions stored in memory and executable by the at least one computing device that, when executed, direct the at least one computing device to: identify a plurality of target placement points for at least one of a plurality of sensors from a plurality of regions of the field, wherein each of the target placement points are identified from a corresponding one of the plurality of regions; generate an initial set of a plurality of potential placement points, wherein the initial set of the potential placement points comprises at least a portion of the plurality of target placement points; and determine the optimal placement of the sensors in the field by performing one or more iterations of a genetic algorithm (GA) routine using the initial set of the plurality of potential placement points until a termination condition is satisfied, wherein the optimal placement is determined by generating a fitness metric for each of the potential placement points in a plurality of generations of potential placement points.

According to a second embodiment, a computer-implemented method for determining an optimal placement of sensors in a field to form a sensor network is described where the method includes identifying a plurality of target placement points for at least one of a plurality of sensors from a plurality of regions of the field, wherein each of the target placement points are identified from a corresponding one of the plurality of regions; generating an initial set of a plurality of potential placement points, wherein the initial set of the potential placement points comprises at least a portion of the plurality of target placement points; and determining the optimal placement of the sensors in the field by performing one or more iterations of a genetic algorithm (GA) routine using the initial set of the plurality of potential placement points until a termination condition is satisfied, wherein the optimal placement is determined by generating a fitness metric for each of the potential placement points in a plurality of generations of potential placement points.

According to a third embodiment, a system for fault detection in an agricultural sensor network is described, where the system includes a plurality of sensors distributed in a plurality of regions of a field; at least one computing device; and program instructions stored in memory and executable by the at least one computing device that, when executed, direct the at least one computing device to: monitor each of the sensors in the agricultural sensor network by collecting data from each of the sensors wirelessly; detect a fault in at least one of the sensors, wherein the fault is identified based at least in part on (a) historical sensor data collected by the at least one of the sensors, and (b) data corresponding to a neighboring one of the at least one of the sensors; and in response to the fault being detected for the at least one of the sensors, generate a metric for the field or for each of the regions of the field, wherein the metric is generated using a measurement inferred for a location of the at least one of the sensors in which the fault is detected.

According to a fourth embodiment, a computer-implement method for fault detection in an agricultural sensor network is described, where the method includes monitoring each of a plurality of sensors in an agricultural sensor network by collecting data from each of the sensors wirelessly; detecting a fault in at least one of the sensors, where the fault is identified based at least in part on (a) historical sensor data collected by the at least one of the sensors, and (b) data corresponding to a neighboring one of the at least one of the sensors; and in response to the fault being detected for the at least one of the sensors, generating a metric for the field or for each of the regions of the field, where the metric is generated using a measurement inferred for a location of the at least one of the sensors in which the fault is detected.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

Figure 1:
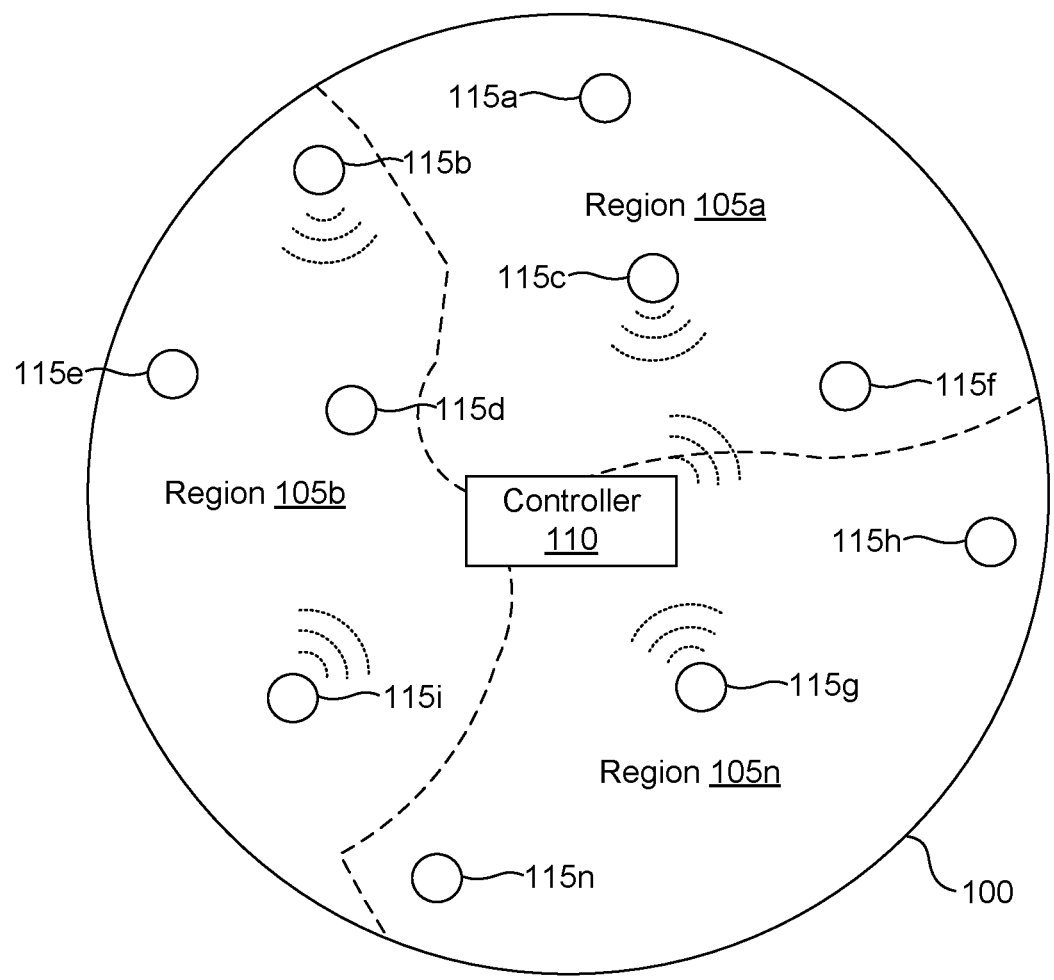
FIG. 1 is a drawing of a field including a controller and field sensors that form a wireless network according to various embodiments of the present disclosure.

The present disclosure relates to optimized sensor deployment and fault detection in the context of agricultural irrigation and other applications. Fresh water is an essential necessity for life; however, it is a resource over-stressed by a growing human population and fluctuation in climates. Notably, agricultural irrigation accounts for approximately two-thirds of global fresh water usage. Thus, decreasing the amount of water used in agricultural irrigation could provide significant reductions in global water usage or allow for greater agricultural productivity with limited water resources.

Traditionally, agricultural irrigation is typically controlled by manual scheduling. Farmers commonly schedule an irrigation system to apply a fixed amount of water to a field or other area at predetermined periods. Further, farmers make determination on whether to irrigate all or a portion of a field based on visual inspections of a plant. For instance, a farmer may look at the color or other condition of a plant to determine whether it has enough water to grow.

The efficiency of water use in agricultural irrigation may be greatly improved, for instance, by incorporating wireless technology into sensors placed at various locations in a field. By placing moisture sensors in a field, irrigation control may be based on an actual soil moisture status (as opposed to a subjective opinion) and unnecessary irrigation and water use can be greatly reduced. However, field sensors must be configured such that they reliably convey soil moisture information with an acceptable accuracy. This is particularly true for agricultural irrigation; however, field sensors are subject to harsh outdoor conditions while farmers are reluctant to spend required capital to purchase and construct a sensor network in their fields.

While sensor-based irrigation methods demonstrate the advantages of using sensors in a field, past methods generally focused on two objectives. First, past methods sought to minimize sensor costs while achieving a certain sensor coverage. Second, past methods sought to gain the most amount of information as possible for sensors given a certain constraint. However, neither method is optimal in agricultural irrigation. For instance, in agricultural irrigation, soil moisture sensor deployment should be based on terrain, soil type(s), plant type, and other characteristics of a crop field. While some fields have relatively homogeneous soils, others can have varying soil types.

Where terrain and soil type of a crop field are heterogeneous in general, the granularity is usually quite coarse. For example, a nominal quarter mile center pivot irrigation machine can cover 120-125 acres of field, where three to five sensors may be sufficient to cover relatively homogeneous soil types and minimal terrain variations. As such, the decision regarding coverage and sensor cost be determined relatively simply. Moreover, if an irrigation controller is installed at the base of a center pivot irrigation machine, a small number of sensors can communicate directly with the controller wirelessly without signal relay.

The use of wireless sensors in agriculture is subject to many technological problems. For instance, wireless sensor networks implemented in agricultural fields are subject to high rates of communication faults or, in other words, the inability to accurately and reliably communicate measurements across a field to a device. Moreover, communication fault tolerances in existing sensor-based systems are not adequate for agricultural sensor networks, which often have complicated sensor network topologies. Placement of the wireless sensors in appropriate portions of a field is critical to avoid high rates of communication faults. Additionally, wireless sensors must be placed in suitable portions of the field such that measurements are actually representative of various regions of the field. As a result, the use of sensor-based networks in agriculture has many technological problems.

Due to the aforementioned deficiencies in the technological field, various embodiments are provided herein for sensor placement and sensor fault detection for agricultural applications. By providing an optimal placement of sensors, accurate measurements can be obtained which may be used in irrigating or otherwise treating a crop, soil, or other item in a field. Additionally, by providing an optimal placement of sensors, communication faults for wireless communication of field data may be significantly reduced, improving overall farming operations.

For instance, given a budget on a number of sensors, various embodiments of the present disclosure provide an optimal sensor deployment scheme using, for example, a failure detection algorithm such that an estimated mean-time-to-failure (MTTF) is maximized. Moreover, sensor redundancy may be implemented to account for unexpected sensor failures while a healthy operation of a sensor network is sustained. Also, according to some embodiments, a fault detection algorithm can be utilized, as will be discussed.

Further, in accordance with various embodiments described herein, a genetic algorithm may be applied to determine an optimal sensor placement for a field or other area. Experimental data are included herein showing that, by utilizing embodiments of the present disclosure, a system mean-time-to-failure is increased as opposed to previous methods. Thus, the embodiments described herein are directed towards improvements in the performance of a sensor network, namely, by reducing sensor communications failure while optimizing sensor placement. In a sensor network that utilizes soil moisture sensors, water usage can be reduced.

In a wireless sensor network, fault detection relates to detecting transient or permanent sensor communication failures. Fault detection methods may be generally classified into one of three categories: centralized, distributed, and hybrid. For instance, in centralized fault detection, a single central node, referring to herein as a central controller, may be positioned at a base station capable of monitoring and analyzing a status of each sensor in a wireless sensor network. In distributed fault detection, fault detection tasks are distributed to each sensor in the network. In hybrid approaches, a combination of distributed and centralized approaches are implemented.

As it is desirable to minimize a number of soil moisture sensors in agricultural irrigation systems, in various embodiments described herein, a centralized fault detection may be employed, where a central controller may be configured to perform fault detection tasks, as will be described. Although methods exist for performing fault detection in wireless sensor networks, generalized techniques are not applicable to agricultural irrigation. For instance, existing methods do not take into account the difficulties and constraints pertaining to soil moisture sensors or other agricultural concerns.

Turning now to the drawings, a field 100 (e.g., a crop field or other agricultural field) is shown in FIG. 1. The field 100 includes, for example, land having various regions 105a . . . 105n (collectively "regions 105"). The regions 105 may be determined by a controller 110 using soil characteristics obtained from sensors 115a . . . 115n positioned through the field 100 as well as using other characteristics. The controller 110, as well as individual one of the sensors 115, may include processing circuitry (e.g., a microprocessor having a hardware processor and memory), soil moisture sensors (or other sensors), as well as transceivers or networking modules (e.g., a wireless fidelity (Wi-Fi), Bluetooth®, or Zig-Bee® module), such that the sensors 115 can communicate with the controller 110 through wireless communications. The controller 110 can include at least one computing device, such as a personal computer or a server, in some embodiments. In alternative embodiments, the controller 110 may include a microprocessor which makes placement of the controller 110 in various locations more suitable (e.g., placement on a mobile irrigation rig or in a box).

In some embodiments, the soil moisture sensors can include, for example, Acclima TDR315, Campbell CS650 or CS655, and Decagon GS1, or other suitable soil moisture sensors. As such, the soil moisture sensors can include a circuit or other processing circuitry capable of obtaining measurements using one or more sensors, and communicate the measurements wirelessly. In some embodiments, the soil moisture sensors may be SDI-12 addressable. Further, in some embodiments, the sensors 115 may be configured to send data through an encrypted security protocol, such as an encrypted form of the ZigBee® protocol.

The sensors 115 may include other types of sensors. For instance, in some embodiments, one or more of the sensors 115 may include a fertility sensor; a salinity sensor; a temperature sensor; a leaf wetness sensor; a plant response sensor; an insect response sensor; a disease response sensor, or other agricultural sensor that may be beneficial in aiding with crop management or crop growth or development.

The sensors 115 may be configured to measure a characteristic of the region 105 (or sub-region) in which it is placed. For instance, in some embodiments, the sensors 115 may include soil moisture sensors 115, although, in other embodiments, other types of sensors 115 may be utilized. The controller 110 may be attached to or otherwise integrated in an irrigation machine, such as a center pivot irrigation machine that moves about a field, as will be described. In additional embodiments, the controller 110 may be integrated in a landscape irrigation system, a subsurface drip irrigation system (e.g., a micro-irrigation system), or other type of irrigation system. In any event, the controller 110 may be configured to control the application of a liquid, such as water, pesticide, plant growth promoter, plant growth inhibitor, or other similar item to crops or other items placed in the field 100. Further, in some embodiments, the controller 110 may include a display device on which a user interface showing an optimal sensor placement may be rendered. Alternatively, in some embodiments, the controller 110 may communicate the optimal sensor placement to another device, such as a mobile device (e.g., a smartphone or tablet) for rendering a user interface in a display of the mobile device, which aids in placement of the sensors 115 at the optimal sensor placement determined by the controller 110, as will be discussed.

It is understood that accurate soil moisture measurements using the sensors 115 are advantageous in the proper management of an automated irrigation system. Ideally, a watering schedule for irrigating crops is implemented based on the input of real-time soil moisture data collected by the controller 110 from each of the sensors 115. Thus, according to various embodiments, the controller 110 may be configured to determine an optimal placement of the sensors 115 in the field 100 such that a wireless network formed by the wireless sensors 115 and/or the controller 110 have a high-degree of reliability and fault-tolerance. The optimal placement of the sensors 115 may be determined by the controller 110 based upon soil information (e.g., physical characteristics of the soil and spatial soil distribution), sensor performance, and/or crop-specific information (e.g., root depth). The controller 110 may be configured to solve for an optimal or near-optimal solution in regards to a highly informative and fault-tolerant placement configuration with reasonable cost and effort.

In some embodiments, the controller 110 can employ a routine that implements an algorithm to determine and/or optimize the optimal placement of the sensors 115, as well as how many sensors 115 are needed and locations as to where the sensors 115 should be deployed. In various embodiments, sensor locations may include coordinates (e.g., longitudinal and/or latitudinal coordinates) as well as a depth at which each sensor 115 should be placed. Further, in some embodiments, the controller 110, through the algorithm, may identify a smallest number of potential locations to deploy the sensors 115 where the sensors 115 will acquire the most-descriptive and representative information for a location in which the sensor 115 is positioned.

To this end, in various embodiments, the controller 110 may have program instructions stored in memory thereon that, when executed, cause the controller 110 to: (1) identify target placement points for the sensors 115 from the regions 105 of the field 100 having different soil or other agricultural characteristics, where each of the target placement points is identified from a corresponding one of the regions 105; (2) generate an initial placement solution set, where the initial placement solution set includes initial placements of the sensors at pseudorandomly generated locations in the field 100; and (3) apply a genetic algorithm using the initial placement solution set to solve for and identify the optimal placement of the sensors 115 in the field 100, wherein the optimal placement is determined using a fitness metric determined for each candidate placement in generations of potential placement sets.

According to various embodiments, after connecting all the target points with edges, the initial placement solution set may include locations on edges between target points. Further, an encoding of the different placements areas may be generated as a string of binary bits. For instance, one bit in a string may correspond to an individual potential location, where "1" indicates that a sensor is deployed at a specific location, and a "0" indicates that no sensor was deployed at that location. The number of "1s" in the string may be less than or equal to a constant value set by an operator according to various constraints or other criteria, such as budget or sensor constraints.

The controller 110 may implement the genetic algorithm by using a randomly generated initial placement solution set and thereafter solving for an optimal solution that includes a set of locations for each sensor 115. A fitness function may be utilized in determining a fitness metric for each potential solution set, wherein the fitness function includes a mathematic model that quantifies a suitability of a potential solution set. The fitness function may be proportional to the cost of the sensors placed and inversely proportional to (1+e to the power of the distance) from one another. The genetic algorithm is discussed in greater detail below. It is understood that the fitness function can include a function of cost, desired fault tolerance, desired quality of information, or other characteristic.

Further, in the vertical dimension, the controller 110 may instruct an operator to deploy one or more sensors 115 at differing depths within a soil profile. In some embodiments, the depths are determined based on the respective crop to be planted within the field 100. For instance, if two sensors 115 are two be deployed at differing depths, the shallower one of the sensors 115 may be positioned at a mid-point depth of the shortest (shallowest) root system while the deeper one of the sensors 115 may be positioned at the mid-point depth of the longest (deepest) root system.

Ultimately, the controller 110 may provide an end-user with a required number of sensors 115 and corresponding locations to deploy each of the sensors 115 so as to achieve a desired quality of information and fault-tolerance in the wireless sensor network. The location can include coordinates, such as a longitude and a latitude, as well as a sensor depth. The end-user can also integrate the sensors 115 into a soil moisture management system or a smart irrigation system that may perform irrigation tasks autonomously based on readings obtained from the sensors 115.

Figure 2:
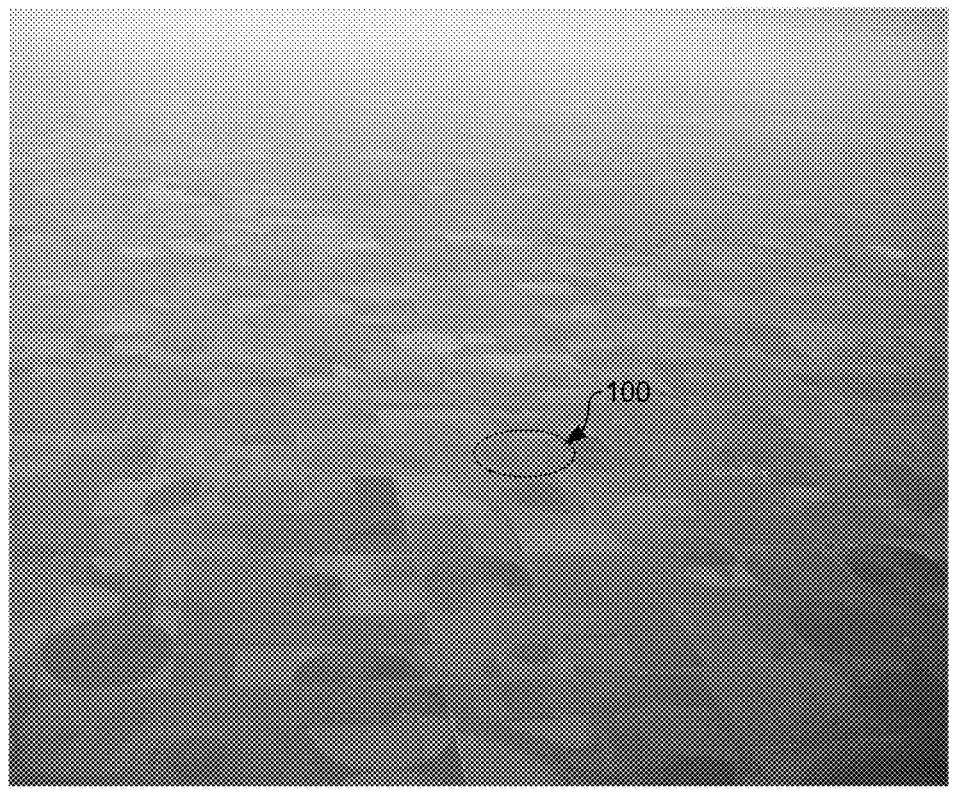
FIGS. 2 and 3 are photographs of example fields having crops planted therein according to various embodiments of the present disclosure.
Figure 3:
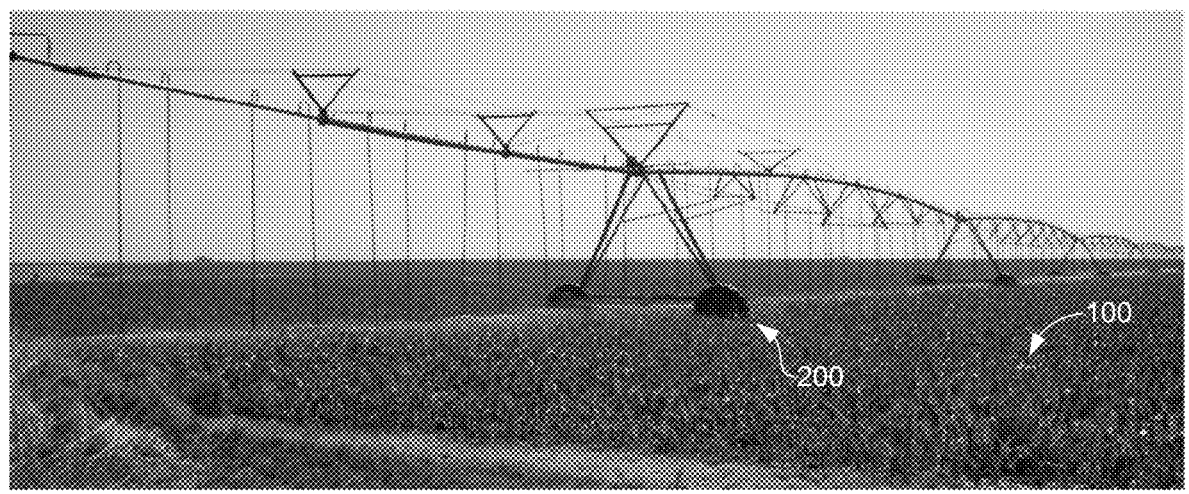

With respect to FIG. 2, a field 100 is shown and, in FIG. 3, a center pivot irrigation machine 300 irrigating a field 100 is shown. Given a constraint on sensor expense, various embodiments for reliably obtaining soil moisture information in a field 100 using a wireless sensor network are disclosed such that wireless soil sensors in the wireless sensor network operate for a sufficiently long time considering sensor failures. Some embodiments include statistically inferring soil moisture levels from functional sensors positioned in a crop field, detecting sensor failure such that information inference is not contaminated by failed sensors, and placing sensors such that a high-quality inference can be obtained given that a certain number of sensors fail.

In a field 100 covered by an irrigation machine (e.g., a circular area covered by a center pivot irrigation machine 300), soil moisture levels may be obtained from every location so that the amount of irrigation water can be efficiently used and applied. Inevitably, soil moisture levels vary at different locations due to different terrain (slope), soil type, crop type, etc. Usually, soil moisture levels are spatially continuous and the variations are spatially correlated. Therefore, it is effective to infer soil moisture levels of an entire field from data of several well-placed sensors 115.

According to various embodiments, soil moisture at a given location may be determined using inferential statistical analysis, which is an analysis capable of inferring properties about a population larger than an observed data set. In other words, a soil moisture level of a field 100 can be determined using a small number of soil moisture sensors 115 placed throughout the field 100. More specifically, given sensor readings $\{z_1, z_2, \ldots, z_n\}$ at n locations, the moisture level $z_t$ at any location t may be inferred by:

$$z_t = \lambda_1 z_1 + \lambda_2 z_2 + \ldots + \lambda_n z_n \quad \text{(eq. 1)},$$

where $\lambda_i$, i=1, 2, ..., n are constant kriging coefficients satisfying the following equation:

$$\sum_{i=1}^{n} \lambda_i = 1 \quad \text{(eq. 2)}$$

The values of kriging coefficients $\lambda_i$ are obtained by solving the following linear system:

$$\lambda_1 \gamma(d_{1,1}) + \lambda_2 \gamma(d_{1,2}) + \ldots + \lambda_n \gamma(d_{1,n}) = \gamma(d_{1,t})$$

$$\lambda_1 \gamma(d_{2,1}) + \lambda_2 \gamma(d_{2,2}) + \ldots + \lambda_n \gamma(d_{2,n}) = \gamma(d_{2,t})$$

$$\lambda_1 \gamma(d_{n,1}) + \lambda_2 \gamma(d_{n,2}) + \ldots + \lambda_n \gamma(d_{n,n}) = \gamma(d_{n,t}) \quad \text{(eq. 3)}$$

where $d_{i,j}$ indicates the distance between locations i and j, and $\gamma(d_{i,j})$ is semivariance (half of the variance of the difference of moisture levels between location i and j).

Figure 4:
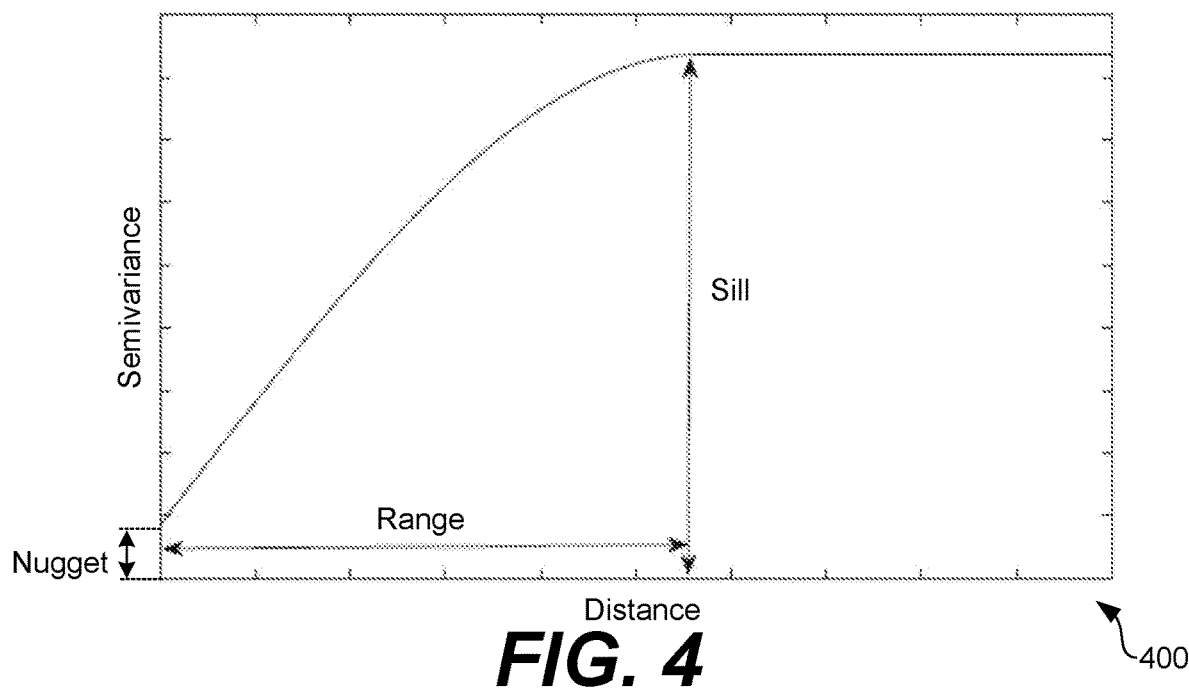
FIG. 4 is a semivariogram according to various embodiments of the present disclosure.

FIG. 4 shows an example of semivariogram 400. The semivariance can be estimated as:

$$\gamma(d) = \frac{1}{2n(d)} \sum_{i=1}^{n(d)} (z(x_i + d) - z(x_i))^2, \quad \text{(eq. 4)}$$

where z is data at a particular location, d is a distance between locations, n(d) is a total number of sample data of paired locations at a distance of d, and $x_i$ and $x_i+d$ refer to the i th pair locations having a distance between the locations d. With reference to the semivariogram 400 of FIG. 4, three important characteristics are shown, namely, a range, a sill, and a nugget. The range may include a maximum distance that two correlated locations can be away from one another. The samples for distance within the range may be spatially correlated. Estimating semivariance using eq. 4 can require a large number of data samples. Another approach may include, for example, applying fitting of a spherical model via:

$$\gamma(d) = \begin{cases} C_0 + C_1 \left( \frac{3d}{2r} - \frac{d^3}{2r^3} \right), & \text{if } d \le r \\ C_0 + C_1, & \text{otherwise} \end{cases} \quad \text{(eq. 5)}$$

where r is the range in the semivariogram 400, $C_0$ and $C_1$ are two constant numbers that can be characterized according to experiment data.

It is beneficial to have reliable sensing, meaning where appropriate system operations are maintained and accurate readings are determined despite faults in a small number of sensors. If a sensor fault can be detected, a kriging-based soil moisture inference can be carried out without using data from the faulty sensor. As such, a high sensing quality can be maintained, even in the presence of a few faults. In addition, a time interval for field repair or sensor battery replacement can be greatly extended.

According to various embodiments, faults can include, for instance, communication or networking errors, battery exhaustion, and permanent device or circuitry failures in sensors positioned throughout a field 100. In some embodiments, fault detection can be centralized. For instance, a controller 110 may act as a central node by being configured to identify faults in the sensors 115 positioned in various regions of the field 100. As such, in some embodiments, the central node may include a centrally-placed controller 110 configured to collect data from all sensors 115 and detect any fault(s) in one or more sensors 115 using sensor data obtained from the sensors 115. In some embodiments, the controller 110 may receive the sensor data from the sensors 115 wirelessly, for example, through the ZigBee® communication protocol, or other suitable communication protocol.

Fault detection can be performed based on spatial correlation among multiple sensors 115 as well as temporal correlation among samples of the same sensor. More specifically, data obtained from a first sensor 115a may be compared with data obtained from a second (neighboring) sensor 115b, as well as recent historical data obtained from the first sensor 115a or the second sensor 115b. A sensor 115 may be determined as faulty if sensor data obtained from the sensor 115 has a significant inconsistency observed from the comparison.

For instance, suppose there are n sensor nodes $\{s_1, s_2, \ldots, s_n\}$ in a field 100. For each sensor s, m of its most recent samples $z_{i,1}, z_{i,2}, \ldots z_{i,m}$, among which $z_{i,m}$ is the latest sample, may be stored in memory by the controller 110 as the samples are received. Each data sample $z_{i,k}$ may be associated with a binary indicator $v_{i,k}$, which is equal to 1 for valid data and 0 for faulty data. The soil moisture at a location of sensor $s_i$ inferred from its neighboring sensors can be calculated using:

$$\tilde{z}_{i,k}^{neighbor} = \frac{\sum_{s_j \in neighbor(s_i)} \lambda_j z_{j,k-1} v_{j,k-1}}{\sum_{s_j \in neighbor(s_i)} \lambda_j v_{j,k-1}}, \quad (eq.\ 6)$$

where λ is a kriging coefficient. Notably, an inference at time step k is based on the data at time step k−1, whose validity has already been evaluated. The prediction of current data at sensor $s_i$ from its history can be determined using:

$$\tilde{z}_{i,k}^{history} = \frac{\sum_{j=1}^{k-1} z_{i,j} v_{i,j}}{\sum_{j=1}^{k-1} v_{i,j}}, \quad (eq.\ 7)$$

where index k is for a current time step. In some embodiments, the controller 110 may be configured to handle at least two distinctive cases. First, the controller 110 may apply a different process when all historical data of sensor $s_i$ are faulty, i.e., the denominator of eq. 7 is 0. In this case, the controller 110 may be configured to ignore historical average data when applying fault detection. Second, the controller 110 may apply a different process when all neighbor sensors are faulty. In some embodiments, the controller 110 may imply an overall system failure, generating an alert that indicates that human intervention may be needed, such as sensor repair or battery replacement.

Except for the special cases, fault detection may be based on a consistency check with a weighted average between $Z_{i,k}^{neighbor}$ and $Z_{i,k}^{history}$ as follows:

$$\tilde{z}_{i,k} = \frac{\sum_{s_j \in neighbor(s_i)} v_{j,k-1}}{V} \tilde{z}_{i,k}^{neighbor} + \frac{\sum_{j=1}^{k-1} v_{i,j}}{V} \tilde{z}_{i,k}^{history}, \quad (eq.\ 8)$$

where $V=\sum_{s_j \in neighbor(s_i)} v_{j,k-1} + \sum_{j=1}^{k-1} v_{i,j}$ is a total number of valid samples from neighbors and the history. Notably, the weights for $Z_{i,k}^{neighbor}$ and $Z_{i,k}^{history}$ are dynamically determined by their numbers of valid samples, respectively. The validity $v_{i,k}$ may be determined by comparing the actual measurement data $z_{i,k}$ and the data $\tilde{z}_{i,k}$ inferred from spatial and temporal correlation via:

$$v_{i,k} = \begin{cases} 0, & \text{if } |\tilde{z}_{i,k} - z_{i,k}| > \theta \cdot z_{i,k} \\ 1, & \text{otherwise} \end{cases}, \quad (eq.\ 9)$$

where θ is a small positive constant value, called a sensitivity threshold.

Figure 5A:
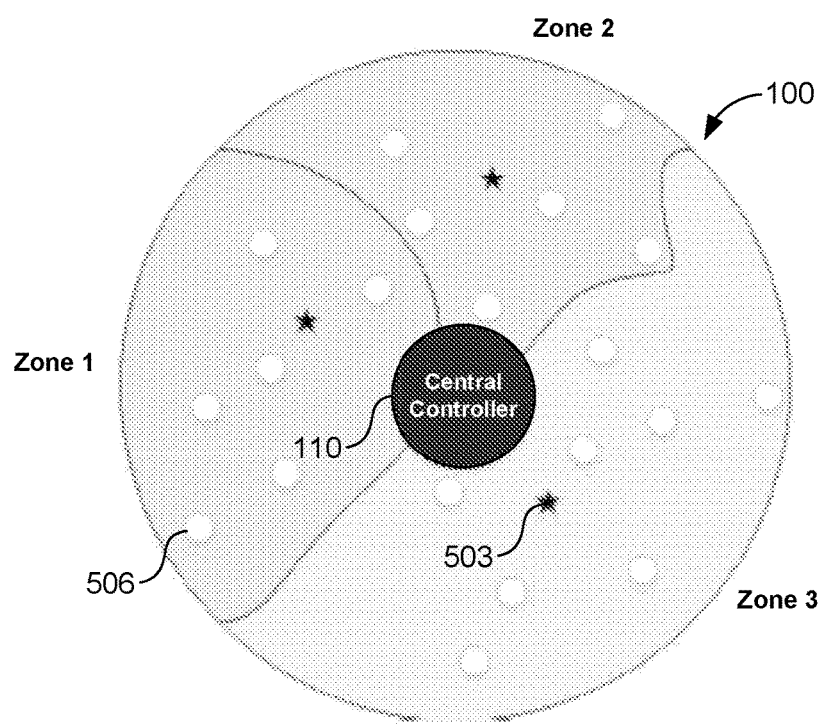
FIGS. 5A-5C are drawings of a field divided into regions or zones, where sensors are placed according to a genetic algorithm and faulty sensors are detected and excluded from information inference according to various embodiments of the present disclosure.
Figure 5B:
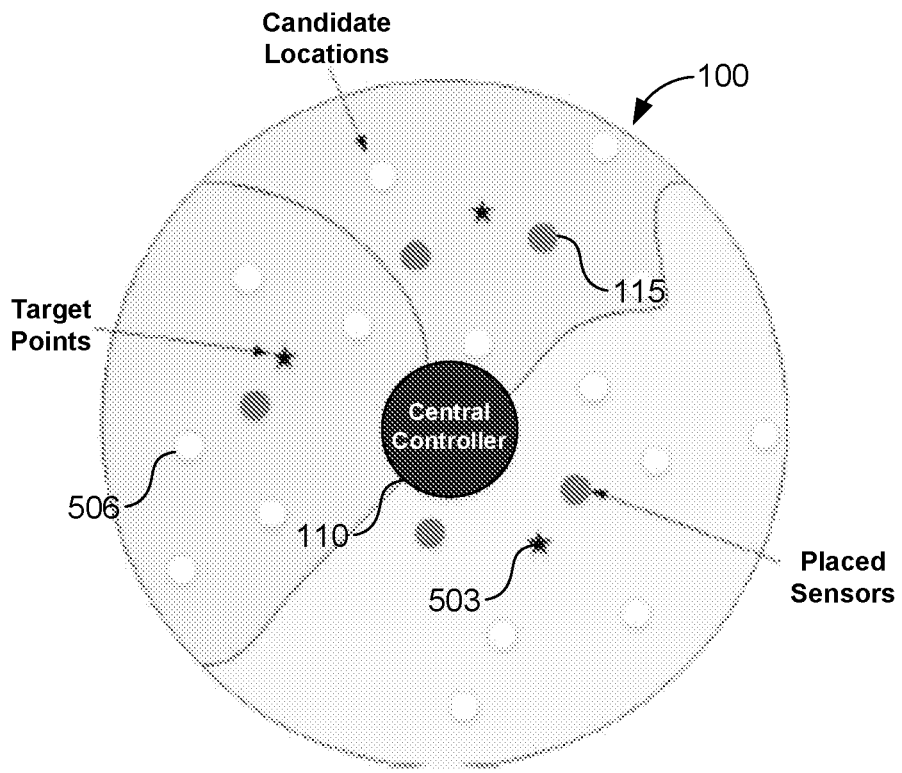
Figure 5C:
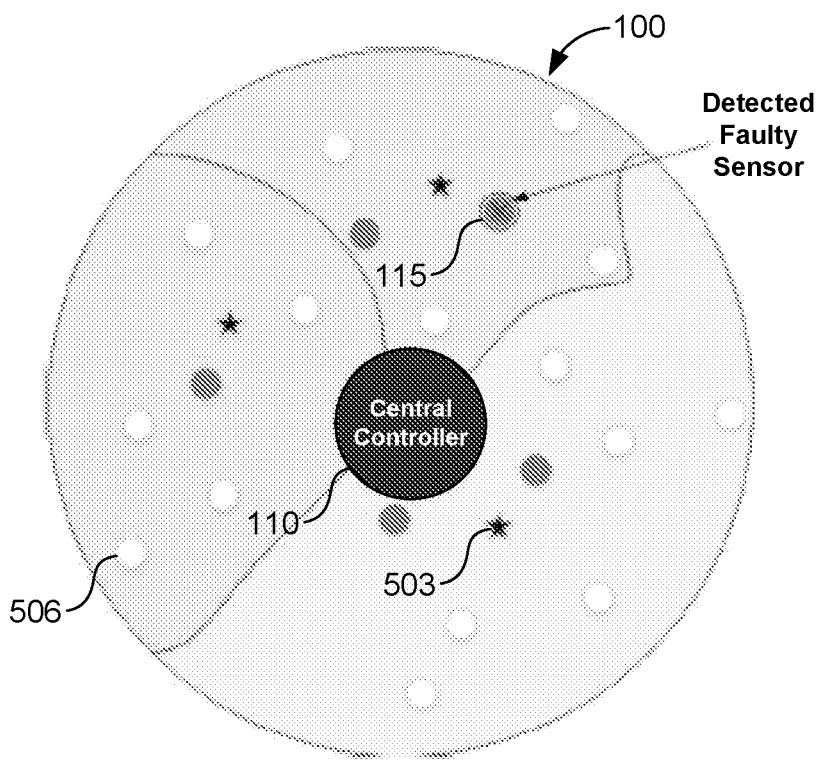

Moving on to FIGS. 5A-5C, a field 100 having a circular shape is shown covered by a center pivot irrigation machine 300. The controller 110 may include, for instance, a networking module (e.g., a wireless networking card) and processing circuitry. In some embodiments, the controller 110 may be physically attached to the center pivot irrigation machine 200 or otherwise integrated with the center pivot irrigation machine 200 such that the controller 110 moves with the center pivot irrigation machine 200. Given a field 100 covered by an irrigation machine 200 and a constraint based on a desired number of sensors 115, sensors 115 may be placed at suitable locations such that sensing data reliably reflects soil moisture levels in the field 100. A field 100 may be divided into multiple zones where each zone has a distinct soil type, terrain shape, or crop type. For instance, as shown in FIG. 5A, a field 100 may be divided into three zones (e.g., Zone 1, Zone 2, and Zone 3) or other amount of zones.

In some embodiments, all zones may be defined such that all the zones intersect at a center of the circle, e.g., where a water source may be located. The soil type, terrain shape, and crop type at a first location in a zone may be very similar to other locations with the same zone. As such, all locations in the same zone may share common irrigation actions, which are decided according to a soil moisture level at a representative location, such as a zone center. The set of zones and, exchangeably the central points of the zones (also referred to as "target points") may be denoted by $Q=\{q_1, q_2, \ldots\}$. A set of candidate sensor locations $P=\{p_1, p_2, \ldots\}$ may be assumed. Although a sensor 115 can be placed anywhere in a field 100, a sufficiently large set P that is regularly distributed is effectively equivalent to considering all points in the field 100. In FIG. 5B, target points 503 are indicated by stars and candidate locations 506 of sensors 115 are illustrated by circles. If the constraint of sensor cost allows up to n sensors 115, the controller 110 may determine a subset of locations $S \subset P$, $|S| \le n$ to place sensors 115 so as to minimize the error between the actual moisture level at zone centers (e.g., target points 503) as well as error inferred from the sensors 115. The instances where $|Q|<n<2|Q|$ may be considered, such that a small degree of redundancy is permitted with limited sensor cost overhead. The placement optimization is mathematically described by:

$$S^* = \arg\min_{S \subset P, |S| \le n} E[err(z_t, \tilde{z}_t(S))], \quad (eq.\ 10)$$

where $z_t$ denotes actual moisture levels at target points, $\tilde{z}_t$ is an estimate of moisture levels at target points according sensor data, err( ) is a certain error function measuring the distance between the actual value and the estimate and E[.] denotes expectation. In some embodiments, this problem may be solved by placing sensors 115 at a center of a zone. However, reliable sensing requires that sensing result is still acceptable despite failures of a small number (k) of sensors.

Assuming S' is a subset of sensors excluding at most k faulty sensors 115, sensor placement may also seek the objective of:

$$S^* = \arg\min_{S' \subset S, S \subset P, |S| \leq n, |S'| > n-k} E[err(z_t, \tilde{z}_t(S'))]. \quad \text{(eq. 11)}$$

Simply placing sensors 115 at zone centers may not necessarily work well for this concern. However, optimizing both eq. 10 and eq. 11 may be difficult, as they require actual soil moisture values at target points. Attempting different placements with actual sensor measurement may be too costly or infeasible. Moreover, sensor placement may consider communication quality. For instance, as soil moisture sensors 115 may communicate directly to the controller 110, sensors 115 may be placed within range of the circle center so as to have reliable communication quality. FIG. 5C shows a detected faulty sensor 115, where any data collected from the faulty sensor 115 may be excluded when the soil moisture of the field 100 is determined, for instance, using statistical inference.

Figure 6:
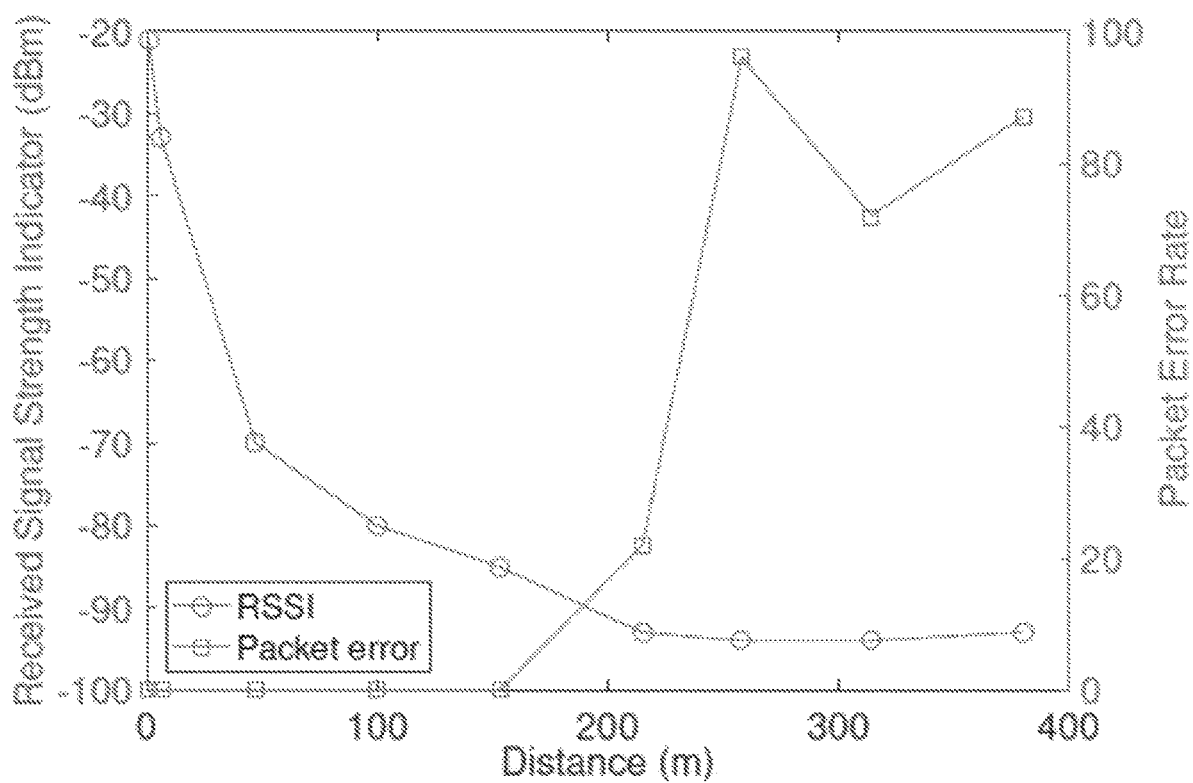
FIG. 6 is a graph illustrating field test results for sensor communication according to various embodiments of the present disclosure.

To quantify a relation between communication quality and distance, an experiment was conducted in the field using an Xbee-PRO ZigBee Module (S2) transmitter manufactured by Digi®. FIG. 6 shows measurement results on packet error rate and received signal strength indicator (RSSI) for different communication distances. As is evident from FIG. 6, the communication quality is excellent when the distance is within 150 meters, marginal for distance range of 150 to 250 meters, and poor for distances beyond 250 meters.

Thus, the controller 115 may be configured to solve a surrogate problem that is largely equivalent to simultaneous consideration of both eq. 10 and eq. 11, while also accounting for communication quality. One observation is that a sensor $s_i$ at location $p_i$ may contribute greatly to estimating a moisture level at target point $q_j$, if the absolute value of kriging coefficient $|\lambda_{i,j}|$ is large. Hence, it may be preferential to choose locations having a relatively large $|\lambda_{i,j}|$ with respect to target points 503. For instance, sensing reliability may require kriging coefficients for all locations be substantially similar to one another. Otherwise, the overall estimation accuracy may have a large degradation when a sensor 115 having a large kriging coefficient fails. Kriging coefficients may be computed more efficiently than, for instance, repeating direct measurements at the field level, as will be discussed.

According to various embodiments, placement of the sensors 115 may be optimized using a genetic algorithm (GA) routine. For instance, a surrogate problem is generally a nonlinear integer programming and is difficult and time-intensive for a computing device to solve. In some situations, a time to solve the surrogate problem is a nondeterministic-polynomial-time-complete problem, or an NP-complete problem. Thus, in various embodiments, an ideal placement of the sensors 115 may be determined by applying a genetic algorithm. The controller 110, or other computing device that determines an optimal sensor placement of the sensors 115, may employ the genetic algorithm to consider sensor-controller communication when determining an ideal placement of the sensors 115. As may be appreciated, the genetic algorithm emulates evolution in a biological sense, where each solution is like a living being. Starting with a set of arbitrary initial solutions or population, new generations of solutions may be obtained through reproduction. Throughout generations of reproductions, good solutions are retained while poor solutions are discarded, similar to "survival of the fittest" in evolution.

To apply the genetic algorithm, the controller 110 may encode each solution as a chromosome. For placement of sensors 115, in some embodiments, each solution may be encoded by a binary string $B = b_{|P|} b_{|P|-1} \ldots b_2 b_1$, where each bit $b_i$, where $i = 1, 2, \ldots, |P|$, is 1 if a sensor is placed at a candidate location $p_i \in P$ and otherwise 0. To satisfy the constraint that no more than n sensors are placed, the controller 110 may require $b_{|P|} + b_{|P|-1} + \ldots b_2 + b_1 \leq n$.

In the genetic algorithm, solutions are evaluated by a fitness function and a solution with a large fitness value may be preferred. To account for the effect of communication quality, we associate each location of a sensor 115 $p_i \in P$ with a communication quality factor $c_i$. The communication quality factor may be determined according to the distance from sensor 115 to controller 110. If $p_i$ is close to the controller 115, the corresponding $c_i$ may have a relatively large value. For one placement solution of sensors 115, $\hat{B}$, a fitness function may be defined as:

$$f(\hat{B}) = \frac{\sum_{i=1}^{|P|} c_i b_i \left( \sum_{j=1}^{|Q|} (\lambda_{i,j}^P)^2 \right)}{\sum_{i=1}^{n} \sum_{j=1}^{|Q|} \left( \lambda_{i,j}^{\hat{B}} - \frac{1}{n} \right)^2}. \quad \text{(eq. 12)}$$

Notably, and $\lambda_{i,j}^P$ and $\lambda_{i,j}^{\hat{B}}$ are quite different, although both indicate a kriging coefficient between sensor location $p_i$ and target point $q_j$. For $\lambda_{i,j}^P$, the kriging coefficient based on all candidate locations in P. In contrast, the kriging coefficient for $\lambda_{i,j}^{\hat{B}}$ is determined from only the n sensor locations in solution $\hat{B}$. In the numerator of the fitness function of eq. 12, $b_i$ may assume a value of either 0 or 1 according to solution $\hat{B}$. Hence, a solution involving large absolute values of kriging coefficients and high communication quality $c_i$ would tend to have a large fitness value. The denominator may make the kriging coefficients from the actual solution as uniform as possible, as the average kriging coefficient for a solution with n sensors is $$\frac{1}{n}.$$

Overall, the fitness function may be used to encourage solutions having a high inference quality (e.g., by having a large $\lambda_{i,j}^P$), a high communication quality (e.g., by having a large $c_i$), and a high reliability (e.g., by having a small $$\left( \lambda_{i,j}^{|B|} - \frac{1}{n} \right)^2 \right).$$

Given an initial population of solutions (e.g., different sets of locations of sensors 115), new solutions of sensor placements may be generated by performing selection, crossover, and mutation processes. A subset of good solutions from a population of a current generation may be identified according the fitness function of eq. 12, and "good" solutions (e.g., solutions having a high fitness value as compared to other solutions) may be carried over to a new generation, as may be appreciated. If there is a set of solutions, $\beta = \{B_1, B_2\}$, and each solution $B_i \in \beta$ is evaluated by fitness function $f(B_i)$, the probability solution $B_i$ that may be carried over to the next generation may be determined using:

$$\frac{f(B_i)}{\sum_{j=1}^{|\beta|} f(B_j)}. \quad \text{(eq. 13)}$$

By using square in the fitness function definition in eq. 12, the difference among solutions may be amplified such that a chance of retaining a good solution is increased. Given a pair of selected solutions, there is a probability of crossover, where different portions of solutions are combined to form a new solution. The probability of crossover is referred to as the crossover rate. If crossover is not performed, the solutions may remain the same, as may be appreciated.

Thereafter, mutation may be performed, where mutation includes applying a random change to a solution. The mutation may be performed with a certain probability, referred to as a mutation rate. Notably, any new solutions must satisfy the constraint $b_{|P|}+b_{|P|+1}+ \ldots +b_2+b_1 \leq n$ or are otherwise removed from the set of solutions. As "better" solutions (e.g., solutions having a high fitness level relative to other solutions) are kept in the selection, the overall solution quality increases over generations as the genetic algorithm is continuously applied. In some embodiments, the controller 110 may apply the genetic algorithm until a maximum fitness solution converges into a single solution and several generations of candidate solutions have been examined. In other embodiments, the controller 110 may apply the genetic algorithm until a predetermined fitness level has been reached. In some embodiments, the controller 110 may apply the genetic algorithm until a predetermined amount of time has elapsed when solving for the optimal locations for placement of the sensors.

Figure 7:
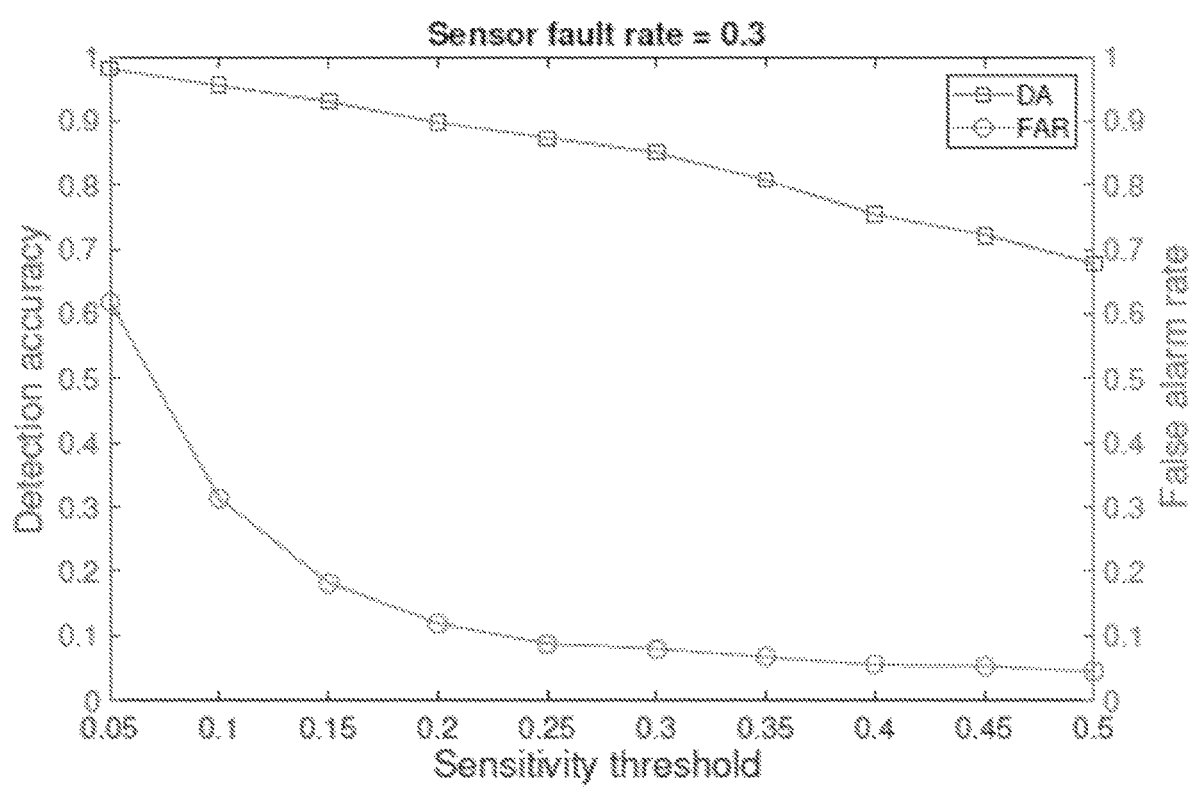
FIG. 7 is a graph illustrating a detection accuracy (DA) and false alarm rate (FAR) over different sensitivity thresholds according to various embodiments of the present disclosure.
Figure 8:
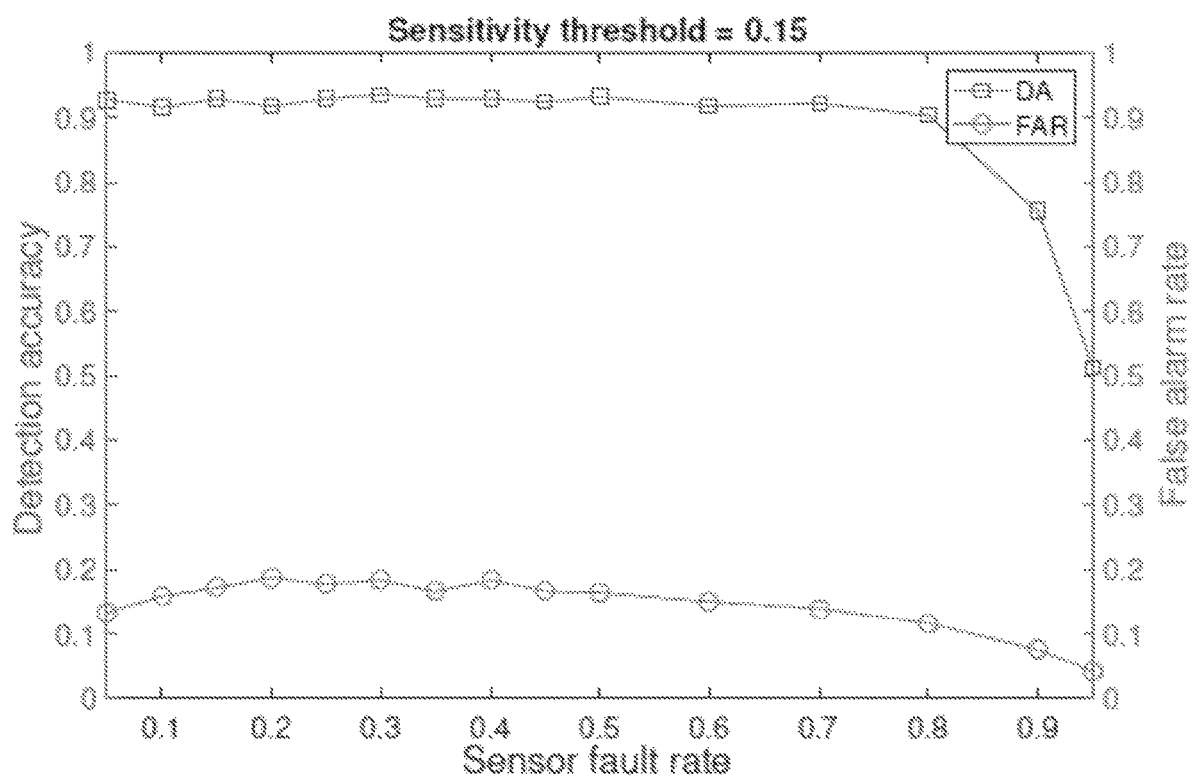
FIG. 8 is a graph illustrating a detection accuracy and false alarm rate over different sensor fault rates according to various embodiments of the present disclosure.

The effectiveness of the embodiments described herein for detecting faulty sensors may be evaluated using a detection accuracy (DA) and a false alarm rate (FAR). Detection accuracy may be defined as the ratio of a number of detected faulty sensors to a total number of faulty sensors while a false alarm rate may be defined as the ratio of a number of fault-free sensors identified as faulty to a total number of fault-free sensors. In FIGS. 6 and 7, detection accuracy (based on a packet error rate) and false alarm rate are shown, respectively, for different sensitivity threshold values ($\theta$) and different sensor fault rates (probability of fault) on an experimental case of ten sensors. From the simulations, $\theta=0.17$ is found to be a good choice as it leads to over 90% detection accuracy with an approximately 10% false alarm rate. FIG. 8 shows an improvement in detection accuracy and false alarm rate over different sensor fault rates.

Figure 9:
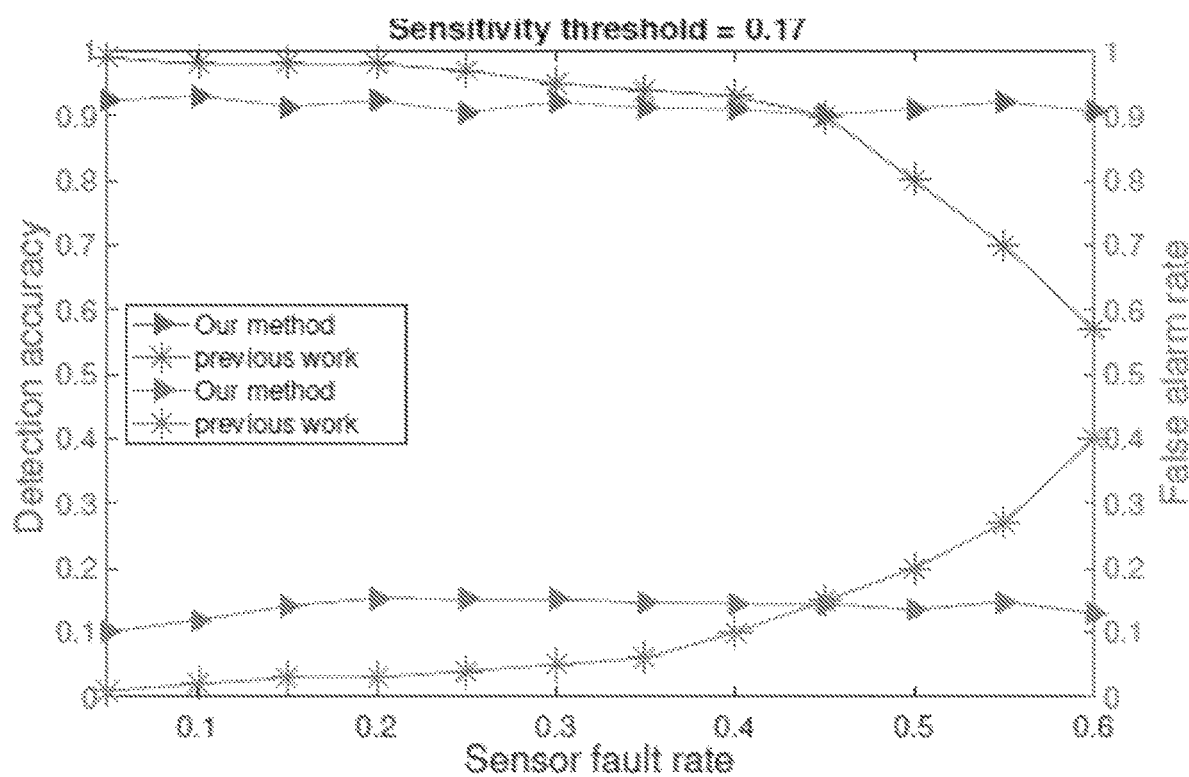
FIG. 9 is a graph illustrating a detection accuracy and false alarm rate over different sensor fault rates according to various embodiments of the present disclosure as compared to prior systems and methods.

With respect to FIG. 9, embodiments described herein for detecting faulty sensors were compared to a distributed fault detection method described in S. Ji, S. F. Yuan, T. H. Ma, and C. Tan, "Distributed fault detection for wireless sensor based on weighted average," in 2nd International Conference on Networks Security Wireless Communications and Trusted Computing, vol. 1, pp. 57-60, IEEE, 2010. As shown in FIG. 9, the detection accuracy and false alarm rate are acceptable even when a fault rate of a sensor 115 is high, unlike prior methods, which quickly become worse and less accurate as the sensor fault rate increases.

In sensor placement simulations, different test cases, as shown in Table 1 below, are explored.

TABLE 1

Test Cases for Sensor Placement

| Case | Sensor Budget | No. of Candidate Locations | No. of Target Points |
|---|---|---|---|
| 1 | 3 | 10 | 2 |
| 2 | 5 | 10 | 3 |
| 3 | 7 | 20 | 4 |
| 4 | 8 | 20 | 5 |

Figure 10A:
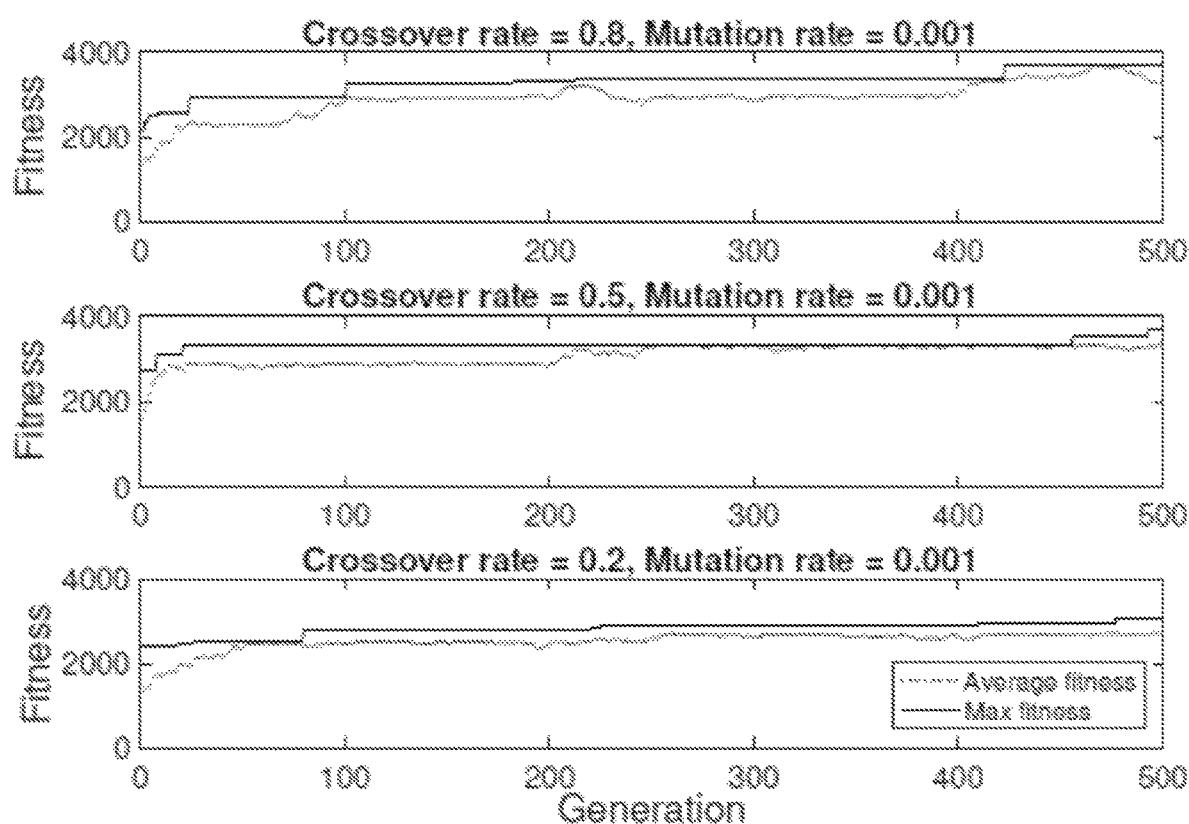
FIGS. 10A and 10B are graphs showing fitness function values of iterations of the genetic algorithm having varying parameters according to various embodiments of the present disclosure.
Figure 10B:
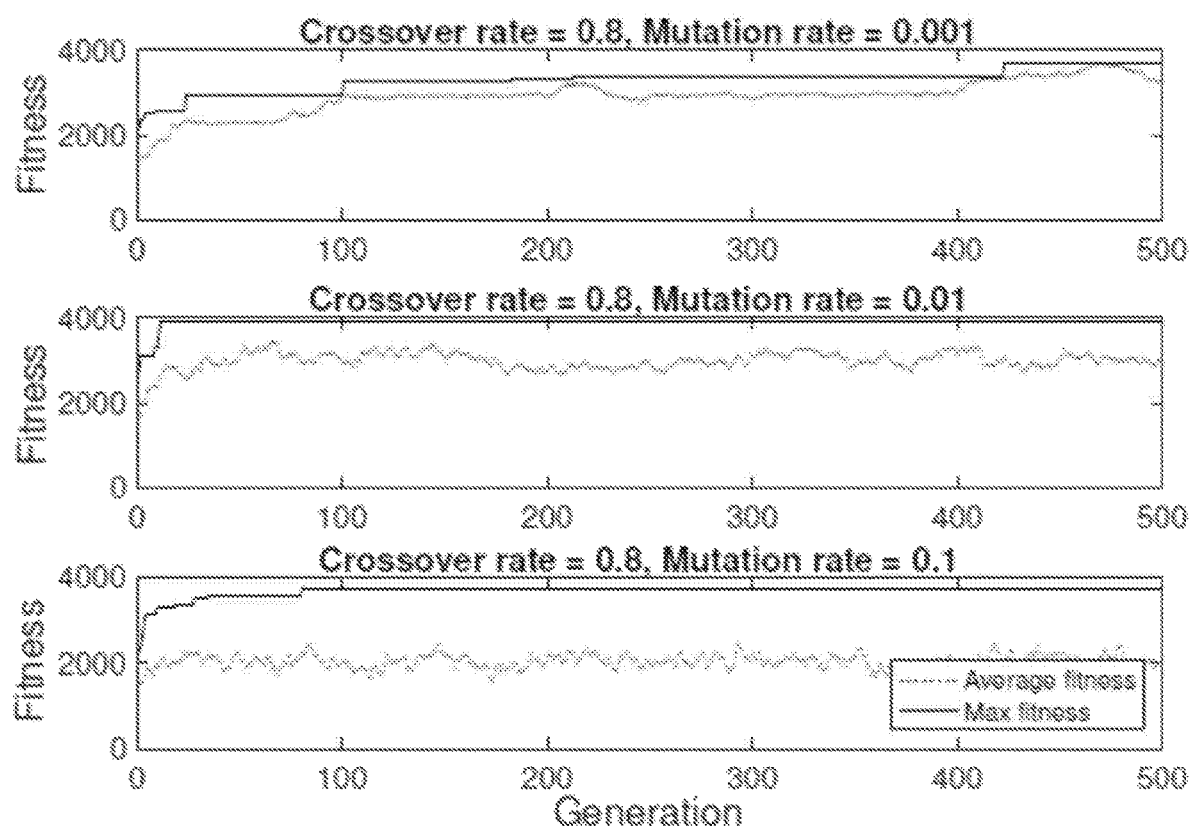

In the various test cases, the population of the genetic algorithm was fixed at twenty or, in other words, a number of solutions for placement of the sensors was set at twenty. The maximum allowable generation was set at five hundred. For one test case, the impact of parameters in the genetic algorithm were studied and the results are shown in FIGS. 10A and 10B. For instance, FIGS. 10A and 10B show that the quickest convergence occurs when the crossover rate is 0.8 and the mutation rate is 0.01.

Embodiments for optimal sensor placement described herein were compared with two other methods, namely, the Naïve method and the heterogeneous point coverage (HPC) method. Specifically, in the Naïve method, for each target point, the nearest location is found to place a sensor which is not blocked by a crop or irrigation machine motion trace. In the heterogeneous point coverage method, it is first assumed that each sensor 115 can cover a certain size of area. The method determines sensor placement such that each target point is covered by at least a certain number of sensors 115.

As embodiments described herein are more focused on reliability, system failure rate in presence of sensor faults were evaluated, particularly in the case of a fault of a single sensor 115, which is generally the most common failure scenario. If there are n sensors, n cases of single sensor fault may be examined. Specifically, a system failure means the sensing error for at least one target point is unacceptably large. The system failure rate is the ratio of the number of system failures over n.

Figure 11A:
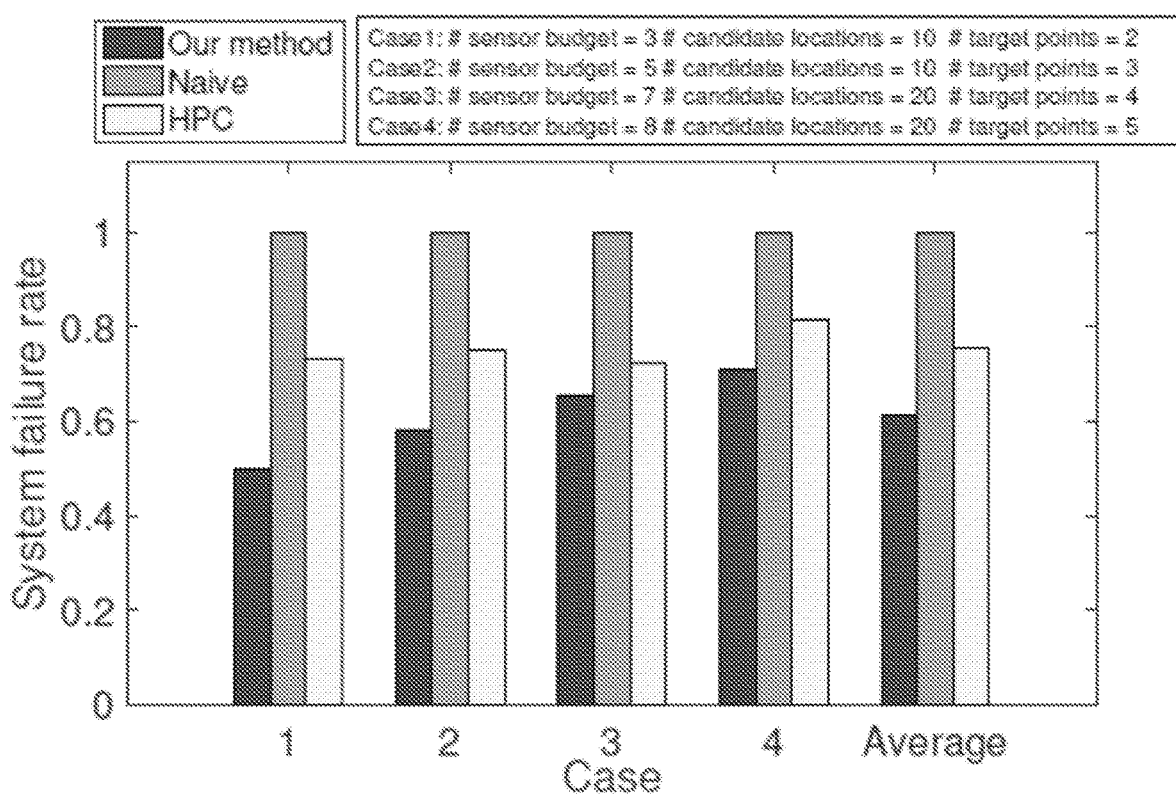
FIG. 11 is a graph illustrating improvements in system failure rate in the presence of a single sensor failure when compared to prior systems and methods according to various embodiments of the present disclosure.
Figure 11B:
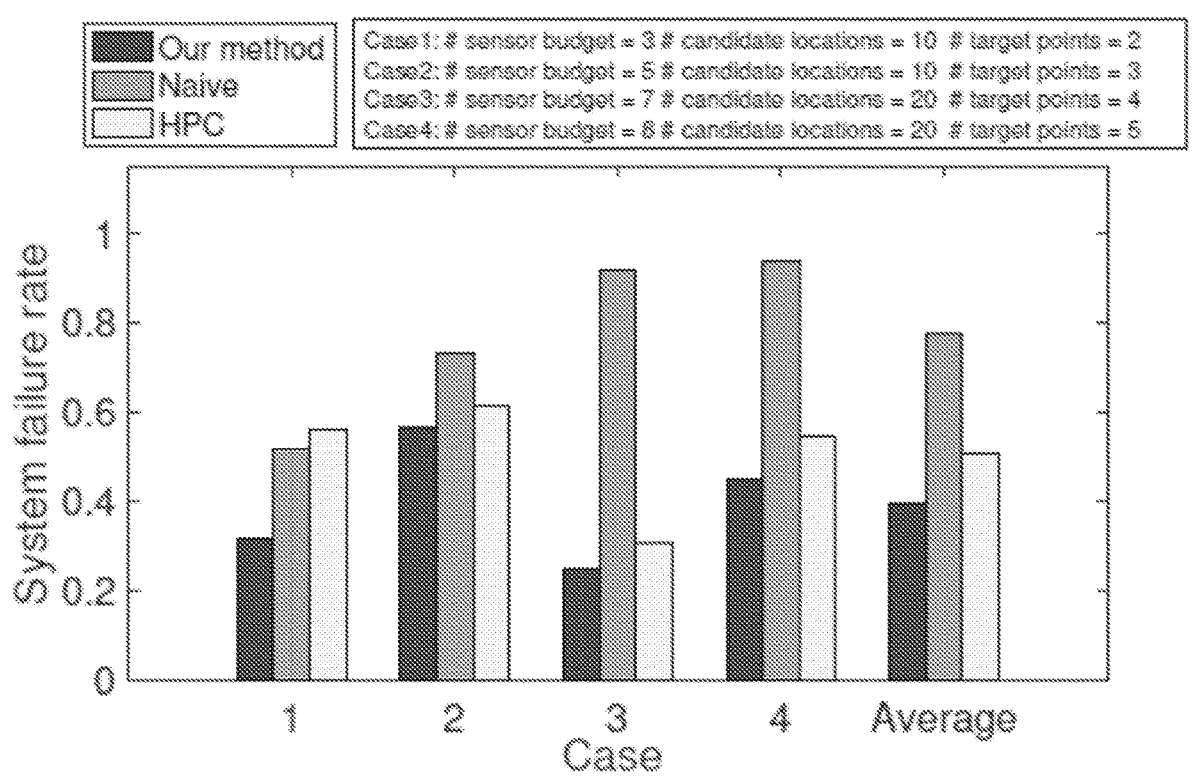

A comparison of embodiments described herein for sensor placement with the Naïve method and the HPC method is shown in FIG. 11A and FIG. 11B. Specifically, in FIG. 11A, data for cases are shown where faulty sensor detection is employed as described herein ("Our method"), which indicates that sensor placement described herein leads to a lower system failure rate than the Naïve method and the HPC method for sensor placement. With respect to FIG. 11B, data are shown as the result of cases that employ the embodiments for faulty sensor detection described herein. Evidently, fault detection can reduce the system failure rate, and again the embodiments described herein significantly outperform the Naïve method and the HPC method.

Figure 12:
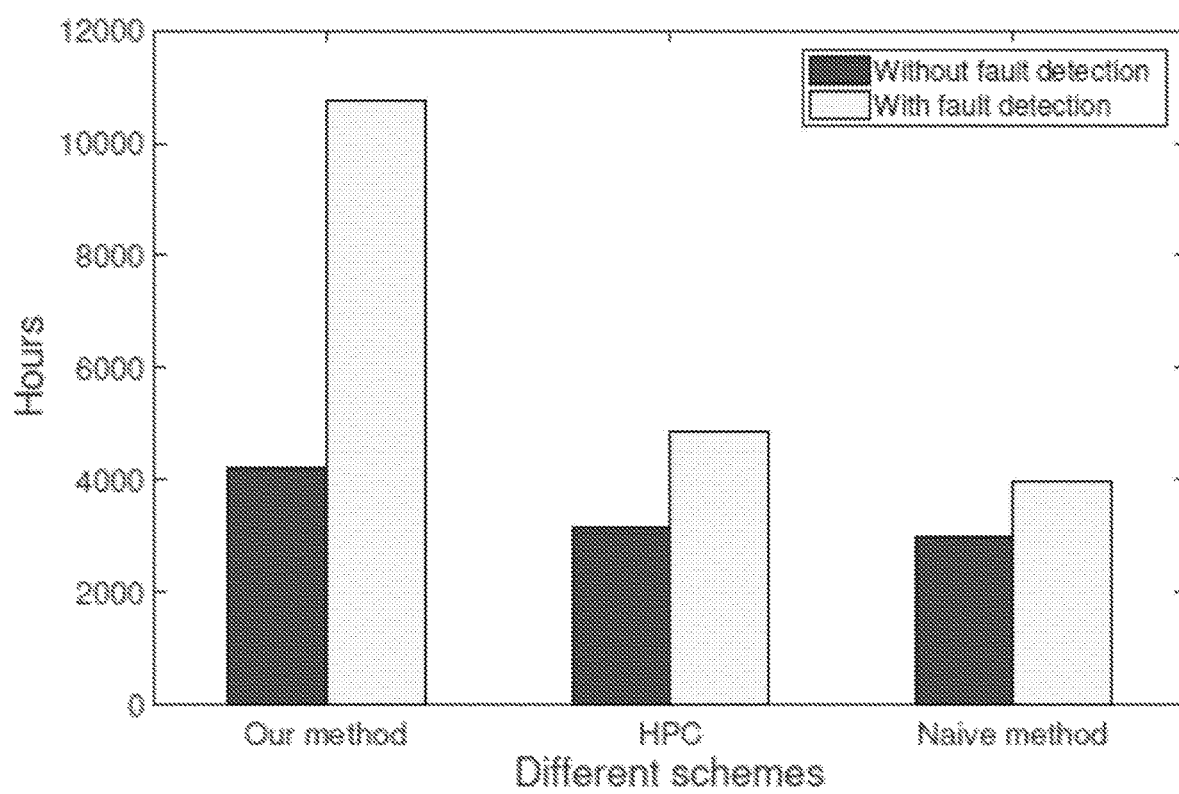
FIG. 12 is a graph illustrating improvements in system mean-time-to-failure (MTTF) when compared to prior systems and methods according to various embodiments of the present disclosure.

In sum, in sensor reliability analysis, an important and intuitive metric is mean-time-to-failure (MTTF), which is the average time that a system or device functions properly from its "new" state to a state of permanent failure (e.g., the system mean lifetime). The system mean-time-to-failure results are obtained by averaging various cases of each method assuming different failure rates for sensors of different ages. In FIG. 12, the mean-time-to-failure has more than doubled by utilizing embodiments described herein for sensor placement along with embodiments described herein for sensor fault detection.

Notably, embodiments described herein in faulty sensor detection and sensor placement are studied for soil moisture sensing in agricultural irrigation, where reliability is a critical concern distinguished from ordinary wireless sensor network designs. However, in additional embodiments, other sensors 115 may be utilized that determine characteristics of a field 100, such as a temperature or humidity sensor, a nutrient sensor, or other similar sensor. It is understood as well that the embodiments for sensor placement and sensor fault detection may be applied in non-agricultural fields 110, such as wireless networking.

With respect to agricultural use, it is shown that spatial and temporal correlation of soil moisture can be effectively used in fault detection and sensor placement based on kriging coefficients. Simulation results from various test cases demonstrate that proposed embodiments described at detail herein significantly reduce a rate of system failure, while improving a mean-time-to-failure by more than two fold compared with Naïve method and HPC sensor placement methods.

The operations of the controller 110 and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc. Such technologies are generally well known by those skilled in the art and, consequently, are not described in detail herein.

Also, the operations of the controller 110 can be implemented by logic or an application that comprises software or program code can be embodied in any non-transitory computer-readable medium for use by or in connection with an instruction execution system such as, for example, a processor in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

Further, any logic or application described herein, including the operations performed by the controller 110, may be implemented and structured in a variety of ways. For example, one or more applications described may be implemented as modules or components of a single application. Further, one or more applications described herein may be executed in shared or separate computing devices or a combination thereof. For example, a plurality of the applications described herein may execute in the same computing device, or in multiple computing devices in a same computing environment. Additionally, it is understood that terms such as "application," "service," "system," "engine," "module," and so on may be interchangeable and are not intended to be limiting.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims and clauses.

Clause 1. A system for determining an optimal placement of sensors in a field to form a sensor network, comprising: at least one computing device; and program instructions stored in memory and executable by the at least one computing device that, when executed, direct the at least one computing device to: identify a plurality of target placement points for at least one of a plurality of sensors from a plurality of regions of the field, wherein each of the target placement points are identified from a corresponding one of the plurality of regions; generate an initial set of a plurality of potential placement points, wherein the initial set of the potential placement points comprises at least a portion of the plurality of target placement points; and determine the optimal placement of the sensors in the field by performing one or more iterations of a genetic algorithm (GA) routine using the initial set of the plurality of potential placement points until a termination condition is satisfied, wherein the optimal placement is determined by generating a fitness metric for each of the potential placement points in a plurality of generations of potential placement points.

Clause 2. The system of clause 1, wherein: each of the target placement points is a central point in one of the regions of the field; and each of the regions of the field have differing agricultural characteristics.

Clause 3. The system of any of clauses 1-2, wherein each of the plurality of sensors is a soil moisture sensor having a network communication module thereon.

Clause 4. The system of any of clauses 1-3, wherein the fitness metric is determined for each of a plurality of potential sensor locations using a fitness function, wherein the fitness function is a function of a communication quality factor ($c_i$) and a predetermined number (n) of the sensors.

Clause 5. The system of any of clauses 1-4, wherein the fitness function determines a fitness metric for each of the sensors, the fitness function comprising:

$$f(\hat{B}) = \frac{\sum_{i=1}^{|P|} c_i b_i \left( \sum_{j=1}^{|Q|} (\lambda_{i,j}^P)^2 \right)}{\sum_{i=1}^{n} \sum_{j=1}^{|Q|} \left( \lambda_{i,j}^{\hat{B}} - \frac{1}{n} \right)^2}.$$

Clause 6. The system of any of clauses 1-5, wherein the optimal placement a longitude and a latitude for placement of each of the plurality of soil sensors in one of the regions of the field.

Clause 7. The system of any of clauses 1-6, wherein the location for placement of each of the plurality of soil sensors comprises a field coordinate and a predetermined depth.

Clause 8. A system for fault detection in an agricultural sensor network, comprising: a plurality of sensors distributed in a plurality of regions of a field; at least one computing device; and program instructions stored in memory and executable by the at least one computing device that, when executed, direct the at least one computing device to: monitor each of the sensors in the agricultural sensor network by collecting data from each of the sensors wirelessly; detect a fault in at least one of the sensors, wherein the fault is identified based at least in part on (a) historical sensor data collected by the at least one of the sensors, and (b) data corresponding to a neighboring one of the at least one of the sensors; and in response to the fault being detected for the at least one of the sensors, generate a metric for the field or for each of the regions of the field, wherein the metric is generated using a measurement inferred for a location of the at least one of the sensors in which the fault is detected.

Clause 9. The system of clause 8, wherein the at least one computing device is implemented in a single controller centrally located with respect to each of the sensors.

Clause 10. The system of any of clauses 8-9, wherein the single controller is attached to a mobile irrigation rig.

Clause 11. The system of any of clauses 8-10, wherein: the at least one of the sensors is a soil moisture sensor; the metric is a soil moisture metric; and the measurement is a soil moisture measurement inferred for the location of the at least one of the sensors in which the fault is detected.

Clause 12. The system of any of clauses 8-11, further comprising program instructions stored in memory and executable by the at least one computing device that, when executed, direct the mobile irrigation rig to perform an irrigation task based at least in part on the soil moisture metric.

Clause 13. The system of any of clauses 8-12, wherein the fault detected in the soil moisture sensor is at least one of: a communication error, battery exhaustion, or electronic device failure.

Clause 14. The system of any of clauses 8-13, wherein the at least one computing device is further directed to determine a validity of the measurement obtained from the at least one of the sensors, wherein the validity of the measurement is determined by comparing actual measurement data obtained from the at least one of the sensors to data inferred from a spatial correlation and a temporal correlation.

Clause 15. The system of any of clauses 8-14, wherein the fault in the at least one of the sensors is detected based at least in part on a consistency check with a weighted average of (i) measurements obtained from the neighboring one of the at least one of the sensors, and (ii) measurements obtained from the historical sensor data collected by the at least one of the sensors.

Clause 16. A computer-implemented method for determining an optimal placement of sensors in a field to form a sensor network, comprising: identifying a plurality of target placement points for at least one of a plurality of sensors from a plurality of regions of the field, wherein each of the target placement points are identified from a corresponding one of the plurality of regions; generating an initial set of a plurality of potential placement points, wherein the initial set of the potential placement points comprises at least a portion of the plurality of target placement points; and determining the optimal placement of the sensors in the field by performing one or more iterations of a genetic algorithm (GA) routine using the initial set of the plurality of potential placement points until a termination condition is satisfied, wherein the optimal placement is determined by generating a fitness metric for each of the potential placement points in a plurality of generations of potential placement points.

Clause 17. The computer-implemented method of clause 16, wherein: each of the target placement points is a central point in one of the regions of the field; and each of the regions of the field have differing agricultural characteristics.

Clause 18. The computer-implemented method of any of clauses 16-17, wherein each of the plurality of sensors is a soil moisture sensor having a network communication module thereon.

Clause 19. The computer-implemented method of any of clauses 16-18, wherein the fitness metric is determined for each of a plurality of potential sensor locations using a fitness function, wherein the fitness function is a function of a communication quality factor ($c_i$) and a predetermined number (n) of the sensors.

Clause 20. The computer-implemented method of any of clauses 16-19, wherein the fitness function determines a fitness metric for each of the sensors, the fitness function comprising:

$$f(\hat{B}) = \frac{\sum_{i=1}^{|P|} c_i b_i \left( \sum_{j=1}^{|Q|} (\lambda_{i,j}^P)^2 \right)}{\sum_{i=1}^{n} \sum_{j=1}^{|Q|} \left( \lambda_{i,j}^{\hat{B}} - \frac{1}{n} \right)^2}.$$

Clause 21. The computer-implemented method of any of clauses 16-20, wherein the optimal placement a longitude and a latitude for placement of each of the plurality of soil sensors in one of the regions of the field.

Clause 22. The computer-implemented method of any of clauses 16-21, wherein the location for placement of each of the plurality of soil sensors comprises a field coordinate and a predetermined depth.

Clause 23. A computer-implemented method for fault detection in an agricultural sensor network, comprising: monitoring, using at least one computing device, each of a plurality of sensors in an agricultural sensor network by collecting data from each of the sensors wirelessly; detecting a fault in at least one of the sensors, wherein the fault is detected based at least in part on (a) historical sensor data collected by the at least one of the sensors, and (b) data corresponding to a neighboring one of the at least one of the sensors; and in response to the fault being detected for the at least one of the sensors, generating a metric for the field or for each of the regions of the field, wherein the metric is generated using a measurement inferred for a location of the at least one of the sensors in which the fault is detected.

Clause 24. The computer-implemented method of clause 8, wherein the at least one computing device is implemented in a single controller centrally located with respect to each of the sensors.

Clause 25. The computer-implemented method of any of clauses 8-9, wherein the single controller is attached to a mobile irrigation rig.

Clause 26. The computer-implemented method of any of clauses 8-10, wherein: the at least one of the sensors is a soil moisture sensor; the metric is a soil moisture metric; and the measurement is a soil moisture measurement inferred for the location of the at least one of the sensors in which the fault is detected.

Clause 27. The computer-implemented method of any of clauses 8-11, further comprising directing the mobile irrigation rig to perform an irrigation task based at least in part on the soil moisture metric.

Clause 28. The computer-implemented method of any of clauses 8-12, wherein the fault detected in the soil moisture sensor is at least one of: a communication error, battery exhaustion, or electronic device failure.

Clause 29. The computer-implemented method of any of clauses 8-13, further comprising determining a validity of the measurement obtained from the at least one of the sensors, wherein the validity of the measurement is determined by comparing actual measurement data obtained from the at least one of the sensors to data inferred from a spatial correlation and a temporal correlation.

Clause 30. The computer-implemented method of any of clauses 8-14, wherein the fault in the at least one of the sensors is detected based at least in part on a consistency check with a weighted average of (i) measurements obtained from the neighboring one of the at least one of the sensors, and (ii) measurements obtained from the historical sensor data collected by the at least one of the sensors.

Therefore, the following is claimed:

1. A system for determining an optimal placement of sensors in a field to form a sensor network, comprising:
at least one computing device; and
program instructions stored in memory and executable by the at least one computing device that, when executed, direct the at least one computing device to:
identify a plurality of target placement points for at least one of a plurality of sensors from a plurality of regions of the field, wherein each of the target placement points are identified from a corresponding one of the plurality of regions, each of the target placement points is a central point in one of the regions of the field, and each of the regions of the field have differing agricultural characteristics;
generate an initial set of a plurality of potential placement points, wherein the initial set of the potential placement points comprises at least a portion of the plurality of target placement points; and
determine the optimal placement of the sensors in the field by performing one or more iterations of a genetic algorithm (GA) routine using the initial set of the plurality of potential placement points until a termination condition is satisfied, wherein the optimal placement is determined by generating a fitness metric for each of the potential placement points in a plurality of generations of potential placement points.

2. The system of claim 1, wherein each of the plurality of sensors is a soil moisture sensor having a network communication module thereon.

3. The system of claim 2, wherein the fitness metric is determined for each of a plurality of potential sensor locations using a fitness function, wherein the fitness function is a function of a communication quality factor ($c_i$) and a predetermined number (n) of the sensors.

4. The system of claim 3, wherein the fitness function determines a fitness metric for each of the sensors, the fitness function comprising:

$$f(\hat{B}) = \frac{\sum_{i=1}^{|P|} c_i b_i \left( \sum_{j=1}^{|Q|} (\lambda_{i,j}^P)^2 \right)}{\sum_{i=1}^{n} \sum_{j=1}^{|Q|} \left( \lambda_{i,j}^{\hat{B}} - \frac{1}{n} \right)^2}.$$

5. The system of claim 2, wherein the optimal placement comprises a longitude and a latitude for placement of each of the plurality of soil sensors in one of the regions of the field.

6. The system of claim 5, wherein the optimal placement of each of the plurality of soil sensors further comprises a field coordinate and a predetermined depth.

7. A computer-implemented method for determining an optimal placement of sensors in a field to form a sensor network, comprising:
identifying, by at least one computing device comprising at least one hardware processor, a plurality of target placement points for at least one of a plurality of sensors from a plurality of regions of the field, wherein each of the target placement points are identified from a corresponding one of the plurality of regions, each of the target placement points is a central point in one of the regions of the field, and each of the regions of the field have differing agricultural characteristics;
generating, by the at least one computing device, an initial set of a plurality of potential placement points, wherein the initial set of the potential placement points comprises at least a portion of the plurality of target placement points; and
determining, by the at least one computing device, the optimal placement of the sensors in the field by performing one or more iterations of a genetic algorithm (GA) routine using the initial set of the plurality of potential placement points until a termination condition is satisfied, wherein the optimal placement is determined by generating a fitness metric for each of the potential placement points in a plurality of generations of potential placement points.

8. The computer-implemented method of claim 7, wherein:
each of the plurality of sensors is a soil moisture sensor having a network communication module thereon.

9. The computer-implemented method of claim 8, wherein the fitness metric is determined for each of a plurality of potential sensor locations using a fitness function, wherein the fitness function is a function of a communication quality factor ($c_i$) and a predetermined number (n) of the sensors, the fitness function determining a fitness metric for each of the sensors, the fitness function comprising:

$$f(\hat{B}) = \frac{\sum_{i=1}^{|P|} c_i b_i \left( \sum_{j=1}^{|Q|} (\lambda_{i,j}^P)^2 \right)}{\sum_{i=1}^{n} \sum_{j=1}^{|Q|} \left( \lambda_{i,j}^{\hat{B}} - \frac{1}{n} \right)^2}.$$

10. The computer-implemented method of claim 7, wherein the optimal placement comprises a longitude and a latitude for placement of each of the plurality of soil sensors in one of the regions of the field.

11. The computer-implemented method of claim 10, wherein the optimal placement of each of the plurality of soil sensors further comprises a field coordinate and a predetermined depth.

12. A non-transitory computer readable medium comprising a program executable by at least one computing device, wherein, when executed, the program causes the at least one computing device to at least:

identify a plurality of target placement points for at least one of a plurality of sensors from a plurality of regions of the field, wherein each of the target placement points are identified from a corresponding one of the plurality of regions, each of the target placement points is a central point in one of the regions of the field, and each of the regions of the field have differing agricultural characteristics;

generate an initial set of a plurality of potential placement points, wherein the initial set of the potential placement points comprises at least a portion of the plurality of target placement points; and determine the optimal placement of the sensors in the field by performing one or more iterations of a genetic algorithm (GA) routine using the initial set of the plurality of potential placement points until a termination condition is satisfied, wherein the optimal placement is determined by generating a fitness metric for each of the potential placement points in a plurality of generations of potential placement points.

13. The non-transitory computer readable medium of claim 12, wherein each of the plurality of sensors is a soil moisture sensor having a network communication module thereon.

14. The non-transitory computer readable medium of claim 13, wherein the fitness metric is determined for each of a plurality of potential sensor locations using a fitness function, wherein the fitness function is a function of a communication quality factor ($c_i$) and a predetermined number (n) of the sensors.

15. The non-transitory computer readable medium of claim 14, wherein the fitness function determines a fitness metric for each of the sensors, the fitness function comprising:

$$f(\hat{B}) = \frac{\sum_{i=1}^{|P|} c_i b_i \left( \sum_{j=1}^{|Q|} (\lambda_{i,j}^P)^2 \right)}{\sum_{i=1}^{n} \sum_{j=1}^{|Q|} \left( \lambda_{i,j}^B - \frac{1}{n} \right)^2}.$$

16. The non-transitory computer readable medium of claim 13, wherein the optimal placement comprises a longitude and a latitude for placement of each of the plurality of soil sensors in one of the regions of the field.

17. The non-transitory computer readable medium of claim 16, wherein the optimal placement of each of the plurality of soil sensors further comprises a field coordinate and a predetermined depth.

* * * * *